(12) United States Patent
Tanaka et al.

(10) Patent No.: US 7,728,177 B2
(45) Date of Patent: *Jun. 1, 2010

(54) OPTICALLY ACTIVE 3-METHYLCYCLOPENTADECANONE AND METHOD FOR PRODUCING INTERMEDIATE THEREOF

(75) Inventors: Shigeru Tanaka, Kanagawa (JP); Kenya Ishida, Kanagawa (JP); Hiroyuki Matsuda, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 102 days.

This patent is subject to a terminal disclaimer.

(21) Appl. No.: 11/920,600

(22) PCT Filed: May 17, 2006

(86) PCT No.: PCT/JP2006/309783

§ 371 (c)(1),
(2), (4) Date: Nov. 16, 2007

(87) PCT Pub. No.: WO2006/126428

PCT Pub. Date: Nov. 30, 2006

(65) Prior Publication Data

US 2009/0124826 A1 May 14, 2009

(30) Foreign Application Priority Data

May 23, 2005 (JP) ............................. 2005-149667

(51) Int. Cl.
*C07C 45/00* (2006.01)
(52) U.S. Cl. .................................................. 568/347
(58) Field of Classification Search .................. 568/347
See application file for complete search history.

(56) References Cited

U.S. PATENT DOCUMENTS 7,479,574 B2 * 1/2009 Matsuda et al. ............. 568/347

2007/0259774 A1* 11/2007 Hartwig et al. ............. 502/155

FOREIGN PATENT DOCUMENTS

EP          1 845 078 A1    10/2007
WO     WO 2006/051595        5/2006

OTHER PUBLICATIONS

Welter et al. Highly Enantioselective Syntheses of Heterocycles via Intramolecular Ir-Catalyzed Allylic Amination and Etherification. Organic Letters, 2005 vol. 7 (7), 1239-1242.*
Graening et al. Iridium-Catalyzed Regio- and Enantioselective Allylation of Ketone Enolates. Journal of the American Chemical Society, 2005, vol. 127(49), 17192-17193.*
van Zijl et al., Advanced Synthesis & Catalysis, 346(4):413-420 (2004).
Boele et al., Chemistry—A European Journal, 10(24):6232-6246 (2004).
Leitner et al., Proceedings of the National Academy of Sciences of the United States of America, 101(16):5830-5833 (2004).
Li et al., Tetrahedron: Asymmetry, 14(18):2687-2691 (2003).
Monti et al., Tetrahedron Letters, 45(37):6859-6862 (2004).
Pena et al., Journal of the American Chemical Society, 124(49:14552-14553 (2002).
Naasz et al., Angewandte Chemie, International Edition, 40(5):927-930 (2001).
Alexakis et al., Tetrahedron: Asymmetry, 15(14):2199-2203 (2004).
Scafato et al., Tetrahedron: Asymmetry, 14(24):3873-3877 (2003).
Y.H. Choi et al., "Copper-catalyzed Conjugate Addition on Macrocyclic, Cyclic, and Acyclic Enones with a Chiral Phosphoramidite Ligand Having a C2-Symmetric Amine Moiety", Tetrahedron:Asymmetry, vol. 13, pp. 801-804 (2002).

* cited by examiner

*Primary Examiner*—Sikarl A Witherspoon
(74) *Attorney, Agent, or Firm*—Peter F. Corless; Christine C. O'Day; Edwards Angell Palmer & Dodge LLP

(57) ABSTRACT

Disclosed is a method for producing an optically active 3-methylcyclopentadecan-1-one which is characterized in that 2-cyclopentadecen-1-one is subjected to a 1,4-conjugate addition reaction of a methyl group by using a methylated organic metal in the presence of a copper catalyst, an enol anion scavenger and a specific optically active phosphoramidite for obtaining an optically active 3-methyl-1-cyclopentadecene derivative, and then the thus-obtained 3-methyl-1-cyclopentadecene derivative is subjected to a solvolysis.

4 Claims, No Drawings

OPTICALLY ACTIVE 3-METHYLCYCLOPENTADECANONE AND METHOD FOR PRODUCING INTERMEDIATE THEREOF

TECHNICAL FIELD

The present invention relates to a method for producing an optically active 3-methylcyclopentadecanone and an intermediate thereof. The present invention also relates to a novel optically active ligand used in the production of optically active 3-methylcyclopentadecane or an intermediate thereof.

BACKGROUND ART

In recent years, with a people's growing interest in nature, as for fragrances, those of high preference, which characteristically evoke the image of natural environment, are attracting attention.

Musk is a product obtained by drying the secretion of the musk gland of male musk deer, and has been highly valued since ancient times, as a fragrance or as a natural medicine. Musks having strong scent have been considered as good products, but today, products containing 2% or more of muscone are considered as better products. Musk deer is an animal of family Moschidae, inhabiting a region extending from the mountainous area in Himalaya to the inland China, and currently importation and exportation of the animal is banned under the Washington Convention. Accordingly, only natural musk that was imported prior to the Washington Convention can be used, and unless artificial breeding of musk deer is achieved successfully, natural musk cannot be put into use in the future.

3-Methylcyclopentadecanone (hereinafter, may be referred to as muscone), which is an ingredient of musk, is one species of typical musk-based fragrances, and it is known that there are differences in the scents depending on the configuration of the methyl group. The optically active isomers of muscone, the (R)-(−)-isomer and the (S)-(+)-isomer, are both useful as fragrances, but the (R)-(−)-isomer has stronger and richer scent compared to the (S)-(+)-isomer. For example, while the (S)-(+)-isomer has a threshold value of 223 ppb, the (R)-(−)-isomer has a threshold value of 61 ppb, and thus the (R)-(−)-isomer is reported to be superior (see Non-Patent Document 1).

From the aspect of activity as well as from the aspects of a growing interest in nature and environment, the interest in (R)-isomers which are excellent in biodegradability is growing, and there has been a demand not for racemates, but for optically active isomers. Furthermore, a number of methods for the optical resolution of racemates have been studied (see, for example, Patent Document 1), but in this method, generation of (S)-isomers is unavoidable. Therefore, a study of the method for selectively producing the (R)-isomer of muscone has been extensively carried out. A method of producing the (R)-isomer using an optically active raw material (see, for example, Patent Document 2), a method of subjecting 3-methyl-2-cyclopentadecen-1-one to asymmetric hydrogenation (see Patent Document 3), and the like have been developed. Then, alkylation resulting from 1,4-addition reaction of α,β-unsaturated ketone by an alkylating agent such as dimethylzinc has been reported (see Patent Document 4), and attention has been focused on the methylation of 2-cyclopentadecen-1-one. In recent years, there have been reports on the method for stereoselective production of muscone of the (R)-isomer through a reaction of 1,4-conjugate addition of a methyl group with respect to 2-cyclopentadecen-1-one. As an example of the method, it has been reported that favorable results can be obtained by using a chiral auxiliary having a bornane skeleton during the synthesis (Non-Patent Document 2). Further, as another example, methods of using various phosphite compounds as ligand are also known (Non-Patent Document 3). In addition to these examples, there are reports on the production of optically active muscone using a complex of copper and a ligand such as mesomer-derived 4-(cis-2,6-dimethylpiperidine)-(R)-dinaphthodioxaphosphepine (Patent Document 5), synthesis of (R)-muscone in which asymmetric methylation by means of dimethylzinc is performed by making use of deoxycholic acid, and a phosphite compound having a binaphthyl group as the chiral base, as optically active ligands, and combining these with a copper catalyst (Non-patent Document 4), and the like.

Moreover, under such circumstances, new methods for the preparation of the raw material, 2-cyclopentadecen-1-one have also been developed (see Patent Document 6).

[Patent Document 1] Japanese Patent Application Laid-open No. 2005-8555
[Patent Document 2] Japanese Patent Application Laid-open No. 2002-30022
[Patent Document 3] Japanese Patent Application Laid-open No. 6-192161
[Patent Document 4] Japanese Patent Application National Publication No. 2001-316309
[Patent Document 5] Korean Patent Application Laid-open No. 2000-49811
[Patent Document 6] Japanese Patent Application National Publication No. 2001-226306
[Non-Patent Document 1] W. Pickenhagen et al., ACS SYMPOSIUM SER. 388 Flavor Chemistry, 1989, p. 151
[Non-Patent Document 2] J. Chem. Soc. Perkin Trans. I, 1193, (1992)
[Non-Patent Document 3] Synlett, 1999, No. 11, 1181
[Non-Patent Document 4] Tetrahedron: Asymmetry, 15 (2004) 2533

DISCLOSURE OF THE INVENTION

Problems to be Solved by the Invention

Nevertheless, in the methods of related art, when the reactions are performed at high concentrations, there are problems such as that side products of high molecular weights are generated, thus not resulting in satisfactory yields, that the production costs rise depending on reaction conditions such as cryogenic temperature, low concentration, or extended reaction time, and the like. Furthermore, there is also a problem that large amounts of catalyst need to be used in order to achieve high optical purity. Therefore, the present invention addresses the problems by providing a practical method for producing optically active muscone using a relatively small amount of catalyst, without employing the reaction conditions such as cryogenic temperature or low concentration.

Means for Solving the Problems

The inventors of the present invention devotedly and repeatedly conducted studies to solve the above-described problems, and as a result, found that when 2-cyclopentadecen-1-one is subjected to an asymmetric methylation reaction in the presence of a copper catalyst and an optically active ligand, an optically active enol derivative is formed by trapping the enol anions that are generated as a reaction intermediate using an appropriate enol anion scavenger, which enol derivative allows the asymmetric methylation reaction to be performed avoiding cryogenic temperature and suppresses the generation of side products, and that, by subsequently subjecting the enol derivative to solvolysis according to a standard method, a desired optically active muscone can be obtained at a high concentration and at a high yield. Thus, the inventors completed the present invention.

Furthermore, the inventors of the present invention found a novel catalyst and a novel optically active ligand compound for this method.

That is, the present invention relates to a method for producing optically active 3-methylcyclopentadecanone, the method comprising reacting 2-cyclopentadecen-1-one with a methylated organic metal in the presence of a copper catalyst, an enol anion scavenger and an optically active phosphoramidite represented by general formula (1):

[Chemical Formula 1]

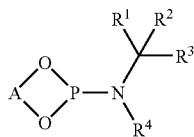

(1)

wherein $R^1$ and $R^2$ each independently represent a hydrogen atom or an alkyl group having 1 to 4 carbon atoms; $R^3$ represents a cycloalkyl group having 3 to 10 carbon atoms which may be substituted, or an aryl group which may be substituted; $R^4$ represents an alkyl group having 1 to 10 carbon atoms, a cycloalkyl group having 3 to 10 carbon atoms which may be substituted, an aryl group which may be substituted, or an aralkyl group which may be substituted; and A represents an optically active biaryldiyl group, to perform a reaction of 1,4-conjugate addition of a methyl group, thus to produce an optically active 3-methyl-1-cyclopentadecene derivative represented by general formula (2):

[Chemical Formula 2]

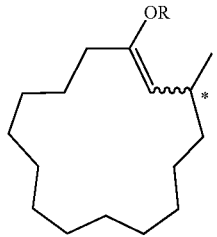

(2)

wherein R represents an enol anion scavenger residue; * represents an asymmetric carbon atom; and the broken line in the formula represents that the compound is a cis-isomer, a trans-isomer or a mixture thereof, and subjecting the derivative to solvolysis.

More particularly, the present invention relates to a method for producing optically active 3-methylcyclopentadecanone, wherein the optically active 3-methylcyclopentadecanone to be produced is 3-(R)-methylcyclopentadecanone.

Furthermore, the present invention relates to a method for producing an optically active 3-methyl-1-cyclopentadecene derivative represented by general formula (2):

[Chemical Formula 4]

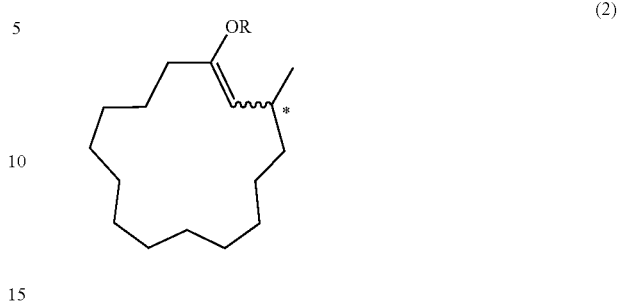

(2)

wherein R represents an enol anion scavenger residue; * represents an asymmetric carbon atom; and the broken line in the formula represents that the compound is a cis-isomer, a trans-isomer or a mixture thereof, the method comprising performing a reaction of 1,4-conjugate addition of a methyl group to 2-cyclopentadecen-1-one by means of a methylated organic metal, in the presence of a copper catalyst, an enol anion scavenger and an optically active phosphoramidite represented by general formula (1):

[Chemical Formula 3]

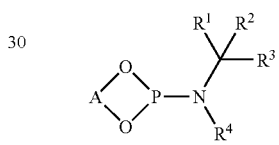

(1)

wherein $R^1$ and $R^2$ each independently represent a hydrogen atom or an alkyl group having 1 to 4 carbon atoms; $R^3$ represents a cycloalkyl group having 3 to 10 carbon atoms which may be substituted, or an aryl group which may be substituted; $R^4$ represents an alkyl group having 1 to 10 carbon atoms, a cycloalkyl group having 3 to 10 carbon atoms which may be substituted, an aryl group which may be substituted, or an aralkyl group which may be substituted; and A represents an optically active biaryldiyl group.

Furthermore, the present invention relates to a compound represented by the following general formula (1'):

[Chemical Formula 5]

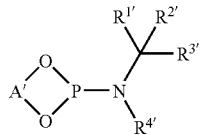

(1')

wherein $R^{1'}$ and $R^{2'}$ each independently represent a hydrogen atom or an alkyl group having 1 to 4 carbon atoms; $R^{3'}$ represents a cycloalkyl group having 3 to 10 carbon atoms which may be substituted, or an aryl group which may be substituted; $R^{4'}$ represents a 1-naphthylmethyl group, a 2-naphthylmethyl group, a 3,4-methylenedioxybenzyl group, a biphenylmethyl group, an anthrylmethyl group, an alkyl group having 1 to 10 carbon atoms, an aryl group which may be substituted, a benzyl group substituted with an alkyl group having 1 to 6 carbon atoms, or a cycloalkyl group having 3 to 10 carbon atoms which may be substituted with or fused with an aryl group; and A' represents a biaryldiyl group. This compound of the present invention is useful as a ligand for catalyst in the selective production of optically active 3-methylcyclopentadecan-1-one.

Also, the present invention relates to an optically active 3-methyl-1-cyclopentadecene derivative represented by the following general formula (2):

[Chemical Formula 6]

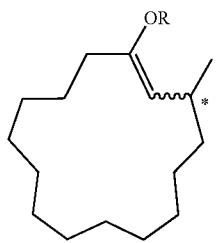

(2)

wherein R represents an enol anion scavenger residue; * represents an asymmetric carbon atom; and the broken line in the formula represents that the compound is a cis-isomer, a trans-isomer or a mixture thereof. The optically active 3-methyl-1-cyclopentadecene derivative of the present invention is useful as an intermediate in the production of optically active 3-methylcyclopentadecan-1-one.

Hereinafter, the present invention will be described in detail.

2-cyclopentadecen-1-one used in the present invention may be exemplified by (E)-2-cylopentadecen-1-one, but the compound is not limited to this, and may also be (Z)-2-cyclopentadecen-1-one, or a mixture of an (E)-isomer and (Z)-isomer. (E)-2-cyclopentadecenone can be produced according to known methods, for example, the methods described in JP-A No. 1-321556, JP-A No. 2001-369422, JP-A No. 2001-226306, and J. Korean Chem., 40, 243 (1996) and the like. In addition, commercially available products may be used.

With regard to the copper catalyst used in the present invention, any of the copper catalysts that have been conventionally used in the 1,4-conjugate addition reaction can be used. Examples of these copper catalysts include copper(II) triflate (Cu(OTf)$_2$), copper(I) triflate (Cu(OTf)), copper(II) trifluoroacetate (Cu(OCOCF$_3$)$_2$), copper(II) acetylacetonate (Cu(acac)$_2$), copper(II) acetate (Cu(OAc)$_2$), copper(II) sulfate (CuSO$_4$), cuprous chloride (CuCl), cupric chloride (CuCl$_2$), cuprous bromide (CuBr), cupric bromide (CuBr$_2$), cuprous iodide (CuI), cupric iodide (CuI$_2$), copper cyanide (CUCN), copper perchlorate (CuClO$_4$), copper naphthenate (Cu(OCOC$_{10}$H$_9$)$_2$), copper(II) tetrafluoroborate (Cu (BF$_4$)$_2$), dilithium tetrachlorocuprate (Li$_2$CuCl$_4$), and the like, and preferable examples are Cu(OTf)$_2$, Cu(OTf) and the like.

Furthermore, the enol anion scavenger used in the present invention may be exemplified by a compound having a group which can bond to the oxygen atom of the enol anion, and a group which leaves at the time of this bonding, and preferred examples of the enol anion scavenger include those compounds which can bond to the hydroxyl group of enol to form enol derivatives such as enol esters, enol carbonates, enol ethers or silyl enol ethers. Specific examples of such enol anion scavenger include an enol anion scavenger represented by the following general formula (3):

$$R^5-X^1 \qquad (3)$$

wherein $R^5$ represents an acyl group, an alkoxycarbonyl group, an alkyl group or a silyl group; and $X^1$ represents a halogen atom, an alkylsulfonyloxy group, an arylsulfonyloxy group, or $OR^6$ (wherein $R^6$ represents an acyl group or an alkoxycarbonyl group), and the like.

The residue of an enol anion scavenger represented by R in the compound represented by general formula (2) according to the present invention, corresponds to the group which can bond to the oxygen atom of the enol anion in the above-mentioned enol anion scavenger, and more specifically, may be exemplified by a group corresponding to $R^5$ of the enol anion scavenger represented by the general formula (3) described above.

For the compound represented by the general formula (3), the acyl group represented by $R^5$ and $R^6$ may be exemplified by an acyl group derived from a saturated or unsaturated, straight-chained or cyclic aliphatic carboxylic acid having 2 to 15 carbon atoms, or an aromatic carboxylic acid having 7 to 15 carbon atoms, that is, an alkylcarbonyl group, an alkenylcarbonyl group, arylcarbonyl group, aralkylcarbonyl group, and the like. These carboxylic acids may be substituted with a substituent such as halogen, an alkoxy group, a lower alkyl group or a nitro group. Specific examples of such acyl group include an acetal group, a propanoyl group, a butyryl group, a pivaloyl group, a valeryl group, an isovaleryl group, a hexanoyl group, an octanoyl group, a decanoyl group, a dodecanoyl group, a cyclohexanoyl group, a benzoyl group, a p-toluoyl group, a p-nitrobenzoyl group, a p-anisoyl group, a p-chlorobenzoyl group, a trifluoroacetyl group, a trichloroacetyl group, an acryloyl group, and the like.

For the compound represented by the general formula (3), the alkoxycarbonyl group represented by $R^5$ and $R^6$ may be exemplified by an alkoxycarbonyl group having 2 to 19 carbon atoms, which may be saturated or unsaturated and straight-chained, branched or cyclic, and the alkyl group, cycloalkyl group or alkenyl group moiety of the alkoxycarbonyl group may be appropriately substituted with a substituent such as halogen, an aryl group or an aralkyl group. Specific examples of such alkoxycarbonyl group include a methoxycarbonyl group, an ethoxycarbonyl group, an n-propoxycarbonyl group, an isopropoxycarbonyl group, an n-butoxycarbonyl group, a tert-butoxycarbonyl group, a pentyloxycarbonyl group, a hexyloxycarbonyl group, a 2-ethylhexyloxycarbonyl group, a lauryloxycarbonyl group, a stearyloxycarbonyl group, an allyloxycarbonyl group, a benzyloxycarbonyl group, a 4-chlorobenzyloxycarbonyl group, a cyclohexyloxycarbonyl group, and the like.

For the compound represented by the general formula (3), the alkyl group represented by $R^5$ may be exemplified by an alkyl group which may be straight-chained, branched or cyclic. Examples of such alkyl group include an alkyl group having 1 to 15 carbon atoms, preferably 1 to 10 carbon atoms, and more preferably 1 to 6 carbon atoms, and specific examples thereof include a methyl group, an ethyl group, an n-propyl group, an isopropyl group, an n-butyl group, a 2-butyl group, an isobutyl group, a tert-butyl group, an n-pentyl group, a 2-pentyl group, a tert-pentyl group, a 2-methylbutyl group, 3-methylbutyl group, a 2,2-dimethylpropyl group, an n-hexyl group, a 2-hexyl group, a 3-hexyl group, a 2-methylpentyl group, a 3-methylpentyl group, a 4-methylpentyl group, a 2-methylpentan-3-yl group, a cyclopropyl group, a cyclobutyl group, a cyclopentyl group, a cyclohexyl group, and the like.

Furthermore, these alkyl group, aryl group and aralkyl group may be appropriately substituted, and examples of the substituent include a hydrocarbon group, an aliphatic heterocyclic group, an aromatic heterocyclic group, an alkoxy group, an alkylenedioxy group, an aryloxy group, an aralkyloxy group, a heteroaryloxy group, a halogen atom, and the like.

Examples of the hydrocarbon group which substitutes the alkyl group include an alkyl group, an alkenyl group, an aryl group, an aralkyl group, and the like.

Such alkyl group may be straight-chained, branched or cyclic, and the alkyl group may be exemplified by an alkyl group having 1 to 15 carbon atoms, preferably 1 to 10 carbon atoms, and more preferably 1 to 6 carbon atoms, or a cycloalkyl group having 3 to 15 carbon atoms, preferably 3 to 10 carbon atoms, and more preferably 3 to 6 carbon atoms. Specific examples thereof include a methyl group, an ethyl group, an n-propyl group, an isopropyl group, an n-butyl group, a 2-butyl group, an isobutyl group, a tert-butyl group, an n-pentyl group, a 2-pentyl group, a tert-pentyl group, a 2-methylbutyl group, a 3-methylbutyl group, a 2,2-dimethylpropyl group, an n-hexyl group, a 2-hexyl group, a 3-hexyl group, a 2-methylpentyl group, a 3-methylpentyl group, a 4-methylpentyl group, a 2-methylpentan-3-yl group, a cyclopropyl group, a cyclobutyl group, a cyclopentyl group, a cyclohexyl group, and the like.

The alkenyl group may be straight-chained or branched, and may be exemplified by an alkenyl group having 2 to 15 carbon atoms, preferably 2 to 10 carbon atoms, and more preferably 2 to 6 carbon atoms. Specific examples thereof include a vinyl group, a propenyl group, a 1-butenyl group, a pentenyl group, a hexenyl group and the like.

The aryl group may be exemplified by a monocyclic, polycyclic or fused cyclic aryl group having 6 to 14 carbon atoms, and specific examples include a phenyl group, a naphthyl group, an anthryl group, a phenanthryl group, a biphenyl group, and the like.

The aralkyl group may be exemplified by a group resulting from the substitution of at least one hydrogen atom of the above-mentioned alkyl group with the above-mentioned aryl group, and for example, is preferably an aralkyl group having 7 to 12 carbon atoms. Specific examples thereof include a benzyl group, a 1-naphthylmethyl group, a 2-naphthylmethyl group, an anthrylmethyl group such as a 9-anthrylmethyl group, a biphenylmethyl group such as a 4-biphenylmethyl group, a 2-phenylethyl group, a 1-phenylpropyl group, a 3-naphthylpropyl group, and the like.

The alipathic heterocyclic group may be exemplified by a 5- to 8-membered, preferably 5- or 6-membered, monocyclic aliphatic heterocyclic group, or a polycyclic or fused cyclic aliphatic heterocyclic group, each containing 2 to 14 carbon atoms and at least one, preferably one to three heteroatoms such as a nitrogen atom, an oxygen atom and a sulfur atom. Specific examples of the aliphatic heterocyclic group include a pyrrolidin-2-one group, a piperidino group, a piperazinyl group, a morpholino group, a tetrahydrofuryl group, a tetrahydropyranyl group, a tetrahydrothienyl group, and the like.

The aromatic heterocyclic group may be exemplified by a 5- to 8-membered, preferably 5- or 6-membered, monocyclic heteroaryl group, or a polycyclic or fused cyclic heteroaryl group, each containing 2 to 15 carbon atoms and at least one, preferably one to three, heteroatoms such as a nitrogen atom, an oxygen atom and a sulfur atom. Specific examples thereof include a furyl group, a thienyl group, a pyridyl group, a pyrimidyl group, a pyrazyl group, a pyridazyl group, a pyrazolyl group, an imidazolyl group, an oxazolyl group, a thiazolyl group, a benzofuryl group, a benzothienyl group, a quinolyl group, an isoquinolyl group, a quinoxalyl group, a phthalidyl group, a quinazolyl group, a naphthyridyl group, a cinnolyl group, a benzoimidazolyl group, a benzoxazolyl group, a benzothiazolyl group, and the like.

The alkoxy group may be exemplified by a group formed from the above-mentioned alkyl group and an oxygen atom bound thereto. For example, an alkoxy group having 1 to 6 carbon atoms may be mentioned, and specific examples thereof include a methoxy group, an ethoxy group, an n-propoxy group, an isopropoxy group, an n-butoxy group, a 2-butoxy group, an isobutoxy group, a tert-butoxy group, an n-pentyloxy group, a 2-methylbutoxy group, a 3-methylbutoxy group, a 2,2-dimethylpropyloxy group, an n-hexyloxy group, a 2-methylpentyloxy group, a 3-methylpentyloxy group, a 4-methylpentyloxy group, a 5-methylpentyloxy group, a cyclohexyloxy group, and the like.

The alkylenedioxy group may be exemplified by an alkylenedioxy group having 1 to 3 carbon atoms, and specific examples thereof include a methylenedioxy group, an ethylenedioxy group, a propylenedioxy group, an isopropylidenedioxy group, and the like.

The aryloxy group may be exemplified by a group formed from the above-mentioned aryl group and an oxygen atom bound thereto. For example, an aryloxy group having 6 to 14 carbon atoms may be mentioned, and specific examples include a phenyloxy group, a naphthyloxy group, an anthryloxy group, and the like.

The aralkyloxy group may be exemplified by a group formed from the above-mentioned aralkyl group and an oxygen atom bound thereto. For example, an aralkyloxy group having 7 to 12 carbon atoms may be mentioned, and specific examples include a benzyloxy group, a 2-phenylethoxy group, a 1-phenylpropoxy group, a 2-phenylpropoxy group, a 3-phenylpropoxy group, a 1-phenylbutoxy group, a 2-phenylbutoxy group, a 3-phenylbutoxy group, a 4-phenylbutoxy group, a 1-phenylpentyloxy group, a 2-phenylpentyloxy group, a 3-phenylpentyloxy group, a 4-phenylpentyloxy group, a 5-phenylpentyloxy group, a 1-phenylhexyloxy group, a 2-phenylhexyloxy group, a 3-phenylhexyloxy group, a 4-phenylhexyloxy group, a 5-phenylhexyloxy group, a 6-phenylhexyloxy group, and the like.

The heteroaryloxy group may be exemplified by a group formed from the above-mentioned aromatic heterocyclic group and an oxygen atom bound thereto. For example, a heteroaryloxy group containing 2 to 14 carbon atoms, and at least one, preferably one to three, of heteroatoms such as a nitrogen atom, an oxygen atom and a sulfur atom, and specific examples thereof include a 2-pyridyloxy group, a 2-pyrazyloxy group, a 2-pyrimidyloxy group, a 2-quinolyloxy group, and the like.

The halogen atom may be exemplified by a fluorine atom, a chlorine atom, a bromine atom, or an iodine atom.

Furthermore, for the compound represented by the above general formula (3), the silyl group represented by $R^5$ may be exemplified by a silyl group having a hydrogen atom on a silicon atom substituted with a substituent such as the above-described hydrocarbon group, and specific examples thereof include a trimethylsilyl group, a triisopropylsilyl group, a tert-butyldimethylsilyl group, a tert-butyldiphenylsilyl group, a triphenylsilyl group, and the like.

In addition, for the compound represented by the above general formula (3), the alkyl group of the alkylsulfonyloxy group represented by $X^1$ may be straight-chained, branched or cyclic, and for example, an alkyl group having 1 to 6 carbon atoms may be mentioned. Specific examples of the alkylsulfonyloxy group include a methanesulfonyloxy group, an ethanesulfonyloxy group, a propanesulfonyloxy group, a butanesulfonyloxy group, a hexanesulfonyloxy group, and the like.

For the compound represented by the general formula (3), the aryl group of the arylsulfonyloxy group represented by $X^1$ may be exemplified by a monocyclic, polycyclic or fused cyclic aryl group having 6 to 14 carbon atoms, and specific examples thereof include a phenyl group, a naphthyl group, an anthryl group, a phenanthryl group, a biphenyl group and the like. These aryl groups may be appropriately substituted with the alkyl group, alkoxy group or halogen atom as described above. Specific examples of the arylsulfonyloxy group include a benzenesulfonyloxy group, a p-toluenesulfonyloxy group, and the like.

For the compound represented by the above general formula (3), the acyl group and alkoxycarbonyl group of $OR^6$ represented by $X^1$ may be exemplified by the acyl group or alkoxycarbonyl group as described above.

To mention some specific compounds used in the present invention as the enol anion scavenger, for example, acid anhydrides such as acetic anhydride, propionic anhydride, butanoic anhydride, pentanoic anhydride, benzoic anhydride, methacrylic anhydride and trifluoroacetic anhydride; acid halides such as acetyl chloride, acetyl bromide, propionyl chloride, propionyl bromide, butyryl chloride, butyryl bromide, pentanoyl chloride, pivaloyl chloride, benzoyl chloride and p-nitrobenzoyl chloride; carbonic acid esters such as dimethyl carbonate, diethyl carbonate, dipropyl carbonate, diphenyl carbonate and dibenzyl carbonate; halogenated silicon derivatives such as trimethylsilyl chloride and triethylsilyl chloride; and the like may be mentioned, but acid anhydrides and carbonic acid esters are preferred.

The optically active phosphoramidite used in the production method of the present invention is an agent acting as a ligand for copper, and has a structure of general formula:

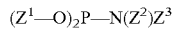

wherein $Z^1$, $Z^2$ and $Z^3$ each independently represent an organic residue. In other words, the compound has a structure in which one ester group of phosphonic acid triester has been amidated by an amine. The optically active phosphoramidite of the present invention may be such that at least one group, or two or more groups among organic residues of $Z^1$, $Z^2$ and/or $Z^3$ are joined together to exhibit asymmetry due to asymmetric carbon atom, or axial asymmetry due to the hindrance to rotation. As preferred optically active phosphoramidite of the present invention, optically active isomers of a compound represented by the following general formula (1):

[Chemical Formula 7]

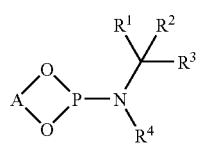

(1)

wherein $R^1$ and $R^2$ each independently represent a hydrogen atom or an alkyl group having 1 to 4 carbon atoms; $R^3$ represents a cycloalkyl group having 3 to 10 carbon atoms which may be substituted, or an aryl group which may be substituted; $R^4$ represents an alkyl group having 1 to 10 carbon atoms, a cycloalkyl group having 3 to 10 carbon atoms which may be substituted, an aryl group which may be substituted, or an aralkyl group which may be substituted; and A represents an optically active biaryldiyl group, or a compound represented by general formula (1'):

[Chemical Formula 8]

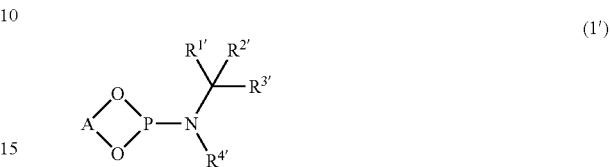

(1')

wherein $R^{1'}$ and $R^{2'}$ each independently represent a hydrogen atom or an alkyl group having 1 to 4 carbon atoms; $R^{3'}$ represents a cycloalkyl group having 3 to 10 carbon atoms which may be substituted, or an aryl group which may be substituted; $R^{4'}$ represents a 1-naphthylmethyl group, a 2-naphthylmethyl group, a 3,4-methylenedioxybenzyl group, a biphenylmethyl group, an anthrylmethyl group, an alkyl group having 1 to 10 carbon atoms, an aryl group which may be substituted, a benzyl group substituted with an alkyl group having 1 to 6 carbon atoms, or a cycloalkyl group having 3 to 10 carbon atoms which may be substituted with or fused with an aryl group; and A' represents a biaryldiyl group, may be mentioned.

In the general formula (1) and general formula (1'), the alkyl group having 1 to 4 carbon atoms for $R^1$, $R^2$, $R^{1'}$ and $R^{2'}$ may be exemplified by a methyl group, an ethyl group, an n-propyl group, an isopropyl group, an n-butyl group, an isobutyl group, a 2-butyl group, or a tert-butyl group.

In the general formula (1) and general formula (1'), the cycloalkyl group of the cycloalkyl group having 3 to 10 carbon atoms which may be substituted, regarding $R^3$ and $R^{3'}$, may be exemplified by a monocyclic, polycyclic, fused cyclic or bridged, saturated or unsaturated aliphatic cyclic group having 3 to 10 carbon atoms, preferably 5 to 10 carbon atoms, and for example, a cyclopentyl group, a cyclohexyl group, a cyclopentenyl group, a cyclohexenyl group and the like may be mentioned. The substituent for these cycloalkyl groups may be exemplified by the aforementioned alkyl group, a halogenated alkyl group in which the alkyl group is substituted with one or more halogen atoms, an aryl group such as a phenyl group, the aforementioned alkoxy group, the aforementioned alkylenedioxy group, a nitro group, a cyano group, a halogen atom, or the like. Also, the substituent for these cycloalkyl groups may be an aryl group such as a phenyl group, which is fused to the cycloalkyl group. Such cycloalkyl group having an aryl group fused therewith may be exemplified by an indan-1-yl group, a tetralin-1-yl group or the like. As a preferred example for $R^3$ in the general formula (1'), a cycloalkyl group having 3 to 10 carbon atoms, preferably 5 to 10 carbon atoms, may be mentioned.

The aryl group of the aryl group which may be substituted, as represented by $R^3$ and $R^{3'}$ in the general formula (1) and general formula (1'), may be exemplified by a monocyclic, polycyclic or fused cyclic aryl group having 6 to 14-carbon atoms. Specific examples of such aryl group include a phenyl group, a naphthyl group, an anthryl group, a phenanthryl group, a biphenyl group, and the like. Examples of the substituent for such aryl group include the aforementioned alkyl group, a halogenated alkyl group in which the alkyl group is substituted with one or more halogen atoms, the aforementioned alkoxy group, the aforementioned alkylenedioxy group, a nitro group, a cyano group, a halogen atom, and the like.

In the general formula (1) and general formula (1'), specific examples of the aryl group which may be substituted, which is represented by $R^3$ and $R^{3'}$, include a phenyl group, an o-tolyl group, an m-tolyl group, a p-tolyl group, a 2-ethylphenyl group, a 4-n-propylphenyl group, a 4-isopropylphenyl group, a 4-tert-butylphenyl group, a 3,5-xylyl group, a 2,4-xylyl group, a 2,6-xylyl group, a 2,6-diisopropylphenyl group, a 2,4,6-trimethylphenyl group, a 2-trifluoromethylphenyl group, a 3-trifluoromethylphenyl group, a 4-trifluoromethylphenyl group, a 3,5-di(trifluoromethyl)phenyl group, a 2-methoxyphenyl group, a 4-methoxyphenyl group, a 2-ethoxyphenyl group, a 4-ethoxyphenyl group, a 4-isopropoxyphenyl group, a 4-tert-butoxyphenyl group, a 2,4-dimethoxyphenyl group, a 2,6-dimethoxyphenyl group, a 2,4,6-trimethoxyphenyl group, a 3,4-methylenedioxyphenyl group, a 3,4-ethylenedioxyphenyl group, a 3,4-propylenedioxyphenyl group, a 3,4-isopropylidenedioxyphenyl group, a 4-nitrophenyl group, a 4-cyanophenyl group, a 2-fluorophenyl group, a 3-fluorophenyl group, a 4-fluorophenyl group, a 3,5-difluorophenyl group, a 3,4,5-trifluorophenyl group, a 2-chlorophenyl group, a 4-chlorophenyl group, a 3,5-dichlorophenyl group, a 2-methoxy-4-methylphenyl group, a 2-methyl-4-methoxyphenyl group, a 2,6-dimethyl-4-methoxyphenyl group, a 3,5-dimethyl-4-tert-butoxyphenyl group, a 1-naphthyl group, a 2-naphthyl group, a 6-methylnaphthyl group, a 6-methoxy-2-naphthyl group, an anthryl group, a phenanthryl group, a biphenyl group, and the like.

In the general formula (1) and general formula (1'), the alkyl group having 1 to 10 carbon atoms represented by $R^4$ and $R^{4'}$ may be exemplified by a straight-chained, branched or cyclic alkyl group, and examples thereof include a methyl group, an ethyl group, an n-propyl group, an isopropyl group, an n-butyl group, an isobutyl group, a 2-butyl group, a tert-butyl group, an n-pentyl group, an n-hexyl group, a cyclopentyl group, a cyclohexyl group, a 2-methylcyclopentyl group, a 2-methylcyclohexyl group, a 2,6-dimethylcyclopentyl group, a 2,6-dimethylcyclohexyl group, a cyclopentylmethyl group, a cyclohexylmethyl group, a (2-methylcyclohexyl)methyl group, a 1-cyclohexylethyl group, a 2-isopropyl-5-methylcyclohexyl group, and the like.

In the general formula (1), the cycloalkyl group of the cycloalkyl group having 3 to 10 carbon atoms which may be substituted, represented by $R^4$, may be exemplified by the cyclic alkyl group among the above-mentioned alkyl groups, which is a monocyclic, polycyclic, fused cyclic or bridged, saturated or unsaturated aliphatic cyclic group having 3 to 10 carbon atoms, preferably 5 to 10 carbon atoms, and examples thereof include a cyclopentyl group, a cyclohexyl group, a cyclopentenyl group, a cyclohexenyl group and the like. Examples of the substituent for these cycloalkyl groups include the above-mentioned alkyl group, a halogenated alkyl group in which the alkyl group is substituted with one or more halogen atoms, an aryl group such as a phenyl group, the aforementioned alkoxy group, the aforementioned alkylenedioxy group, a nitro group, a cyano group, a halogen atom, and the like. Also, the substituents in these cycloalkyl groups may be an aryl group such as a phenyl group, which is fused with the cycloalkyl group, and such cycloalkyl group fused with an aryl group may be exemplified by an indan-1-yl group, a tetralin-1-yl group, or the like.

In the general formula (1'), the cycloalkyl group of the cycloalkyl group having 3 to 10 carbon atoms which may be substituted with or fused with an aryl group, which is represented by $R^{4'}$, may be exemplified by a monocyclic, polycyclic, fused cyclic or bridged, saturated or unsaturated aliphatic cyclic group having 3 to 10 carbon atoms, preferably 5 to 10 carbon atoms, and for example, a cyclopentyl group, a cyclohexyl group, a cyclopentenyl group, a cyclohexenyl group and the like may be mentioned. These cycloalkyl groups may be substituted with or fused with an aryl group such as a phenyl group or a naphthyl group, as a substituent or a ring to be fused. A preferred example of the cycloalkyl group having 3 to 10 carbon atoms which may be substituted with or fused with an aryl group, may be a cycloalkyl group having 5 to 10 carbon atoms which is fused with an aryl group. The cycloalkyl group having 5 to 10 carbon atoms which is fused with an aryl group may be exemplified by an indan-1-yl group, an inden-1-yl group, a tetralin-1-yl group, or the like.

In the general formula (1) and general formula (1'), the aryl group which may be substituted, which is represented by $R^4$ and $R^{4'}$, may be exemplified by the aryl group which may be substituted, which has been described in the description for $R^3$ and $R^{3'}$.

The aralkyl group of the aralkyl group which may be substituted, which is represented by $R^4$ in the general formula (1), may be exemplified by the aralkyl group as described above, and specific examples thereof include a benzyl group, a 1-naphthylmethyl group, a 2-naphthylmethyl group, an anthrylmethyl group such as a 9-anthrylmethyl group, a biphenylmethyl group such as a 2-biphenylmethyl group, a 2-phenylethyl group, a 1-phenylethyl group, a 3-(1-naphthyl)-propyl group, and the like.

The substituent which substitutes these aralkyl groups may be exemplified by the aforementioned alkyl group, the aforementioned alkoxy group, the aforementioned alkylenedioxy group or the like, and these substituents are substituted on the aryl group of the aralkyl group.

Specific examples of the aralkyl group which may be substituted, which is represented by $R^4$ in the general formula (1), include a benzyl group, a 1-phenethyl group, a 1-phenylpropyl group, a 2-methyl-1-phenylpropyl group, a 2-phenethyl group, a 2-methylbenzyl group, a 4-methylbenzyl group, a 4-isopropylbenzyl group, a 4-tert-butylbenzyl group, a 2,4-dimethylbenzyl group, a 2-methoxybenzyl group, a 3-methoxybenzyl group, a 4-methoxybenzyl group, a 4-tert-butoxybenzoyl group, a 3,4-methylenedioxybenzyl group, a 1-naphthylmethyl group, a 2-naphthylmethyl group, a 2-biphenylmethyl group, a 9-anthrylmethyl group, and the like.

Furthermore, specific examples of the benzyl group substituted with an alkyl group having 1 to 6 carbon atoms, which is represented by $R^{4'}$ in the general formula (1') include a 2-methylbenzyl group, a 2-ethylbenzyl group, a 2-isopropylbenzyl group, a 2-tert-butylbenzyl group, a 2-cyclohexylbenzyl group, a 2,4-dimethylbenzyl group, a 2,6-dimethylbenzyl group, a 2-methyl-4-isopropylbenzyl group, and the like.

The biaryldiyl group of A' in the general formula (1') of the present invention is a divalent group having a structure in which two aryl ring structures are directly bound to each other, and the biaryldiyl skeleton may not exhibit optical activity due to axial asymmetry, but it is preferable that the biaryldiyl skeleton exhibits optical activity due to axial asymmetry. Such an aryl ring structure may be exemplified by a monocyclic, polycyclic or fused cyclic 6-membered aromatic ring, preferably a monocyclic or fused cyclic 6-membered aromatic ring, for example, a benzene ring, a naphthalene ring, a phenanthrene ring, or the like. The two aryl rings forming the biaryldiyl group may be different from each other, but it is preferable that the rings are identical.

The optically active biaryldiyl group of A in the general formula (1) of the present invention is the biaryldiyl group described above, in which the biaryldiyl skeleton has become optically active due to axial asymmetry.

An optically active biaryldiyl group indicates that the biaryldiyl skeleton has become optically active due to axial asymmetry, and a substituent on the nitrogen atom being optically active indicates that for example, the alkyl group having an asymmetric carbon atom, of a 2-butyl group, a 1-cyclohexylethyl group, a 1-phenethyl group, a 1-naphthylethyl group or the like has become optically active.

The biaryldiyl group represented by A and A' may be exemplified by a 1,1'-binaphthalene-2,2-diyl group, or the like, and this binaphthyl ring may be substituted with an alkyl group such as a methyl group or a tert-butyl group; an alkoxy group such as a methoxy group or a tert-butoxy group; a trialkylsilyl group such as a trimethylsilyl group, a triisopropylsilyl group or a tert-butyldimethylsilyl group; or a triarylsilyl group such as a triphenylsilyl group.

A preferred example of the biaryldiyl group represented by A and A' in the general formula (1) or general formula (1') of the present invention is a 1,1'-biaryl-2,2'-diyl group which may be substituted, which is represented by the following formula (4):

[Chemical Formula 9]

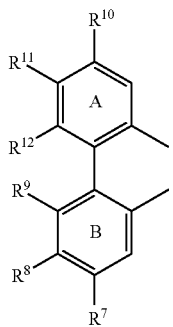

(4)

wherein $R^7$, $R^8$, $R^9$, $R^{10}$ $R^{11}$ and $R^{12}$, which may be identical or different, each represent a hydrogen atom, an alkyl group, an alkoxy group, an acyloxy group, a halogen atom, a haloalkyl group or a dialkylamino group; $R^8$ and $R^9$ may form an alkylene chain which may be substituted, and $R^{11}$ and $R^{12}$ may form an alkylene chain which may be substituted; and ring A and ring B each independently represent a benzene ring, or a ring in which two or more of 6-membered aromatic rings are fused.

The ring A and ring B in the general formula (4) may be exemplified by a benzene ring, a naphthalene ring, a phenanthrene ring, or the like.

The alkyl group of $R^7$ to $R^{12}$ in the general formula (4) may be exemplified by an alkyl group having 1 to 6 carbon atoms which may be straight-chained or branched, such as a methyl group, an ethyl group, an n-propyl group, an isopropyl group, an n-butyl group, an isobutyl group, a sec-butyl group, or a tert-butyl group; and the alkoxy group may be exemplified by an alkoxy group having 1 to 6 carbon atoms which may be straight-chained or branched, such as a methoxy group, an ethoxy group, an n-propoxy group, an isopropoxy group, an n-butoxy group, an isobutoxy group, a sec-butoxy group or a tert-butoxy group. The acyloxy group may be exemplified by a straight-chained or branched alkylcarbonyloxy group having 2 to 6 carbon atoms, such as an acetoxy group or a propanoyloxy group; a halogen-substituted alkylcarbonyloxy group having the alkyl group moiety of the aforementioned alkylcarbonyloxy group substituted with a halogen atom, such as a trifluoroacetoxy group; an arylcarbonyloxy group or aralkylcarbonyloxy group having 7 to 16 carbon atoms, such as a benzoyloxy group; or the like. The halogen atom may be exemplified by a chlorine atom, a bromine atom, a fluorine atom or the like; the haloalkyl group may be exemplified by the aforementioned alkyl group which is substituted with these halogen atoms, for example, a haloalkyl group having 1 to 6 carbon atoms such as a trifluoromethyl group; and the dialkylamino group may be exemplified by an amino group substituted with the aforementioned alkyl group, such as a dimethylamino group or a diethylamino group.

The alkylene chain in the cases where $R^8$ and $R^9$ form an alkylene chain, and where $R^{11}$ and $R^{12}$ form an alkylene chain, is preferably a straight-chained or branched alkylene chain having 3 to 5 carbon atoms, and specifically may be exemplified by a trimethylene group, a tetramethylene group, a pentamethylene group, or the like. Also, the substituent of the alkylene chain which may be substituted may be exemplified by the aforementioned alkyl group, the aforementioned halogen atom, or the like, and specific examples thereof include an alkyl group having 1 to 6 carbon atoms as described above, a fluorine atom, and the like.

For the optically active ligand represented by the general formula (1) of the present invention, the biaryldiyl group of the group A may become an optically active group of (R)-isomer or (S)-isomer due to axial asymmetry, the group $R^1$, group $R^2$, group $R^3$, or the carbon atom to which these groups are attached may become asymmetric to attain optical activity, or both of these biaryldiyl group and the group attached to the nitrogen atom may become asymmetric to attain optical activity.

The compound represented by the general formula (1') of the present invention is not necessarily limited to an optically active isomer, but like the optically active ligand represented by general formula (1) described above, a compound which has become optically active due to the asymmetry of the biaryldiyl group in the general formula (1') and/or the substituent on the nitrogen atom, is preferred.

The optically active ligand represented by general formula (1), or the compound represented by general formula (1') of the invention can be synthesized according to a known method, and for example, can be synthesized by the following scheme according to the methods described in J. Org. Chem., 58, 7313 (1993) and Tetrahedron: Asymmetry, 13, 801 (2002).

[Chemical Formula 10]

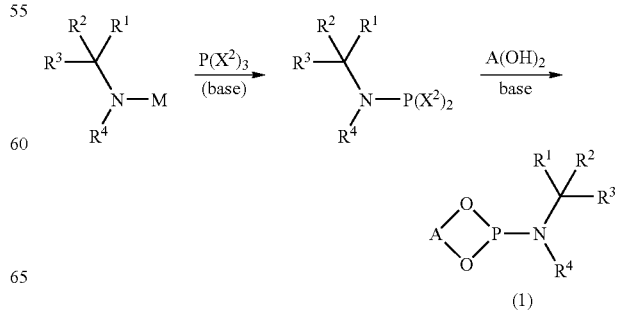

(1)

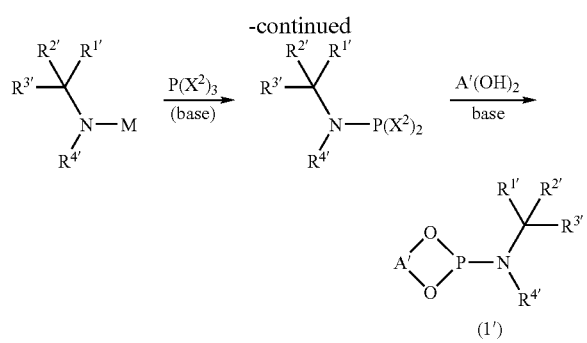

M = H, alkali metal
X² = leaving group wherein $R^1$ to $R^4$, $R^{1\prime}$ to $R^{4\prime}$, A and A' have the same meanings as defined above; M represents a hydrogen atom or an alkali metal atom; and $X^2$ represents a leaving group.

Specifically, the synthesis is carried out in two steps, in which a secondary amine compound or an alkali metal amide thereof is reacted with a phosphorus compound having a leaving group to prepare a compound having a phosphorus-nitrogen bonding (first step), and the resultant is reacted with biaryldiol in the presence of a base (second step). Here, when an optically active isomer is used as the secondary amine compound used, an optically active ligand in which the substituent on the nitrogen atom is optically active can be obtained, and also, when optically active biaryldiol of (R)-isomer or (S)-isomer is used as the biaryldiol, a ligand in which the biaryl skeleton is optically active can be obtained. Of course, it is needless to say that when optically active isomers are used for both the secondary amine compound and the biaryldiol, a compound in which both of the skeletons are optically active can be obtained.

The alkali metal of the alkali metal amide, which is represented by M in the scheme shown above, may be exemplified by lithium, sodium, potassium, rubidium, cesium or the like, but lithium or sodium is preferred.

The method of producing the alkali metal amide is performed by subjecting the secondary amine compound to the action of an alkali metal or an alkali metal compound. The alkali metal compound used may be exemplified by an alkali metal hydride such as sodium hydride, lithium hydride or potassium hydride; an alkyllithium such as methyllithium, n-butyllithium, 2-butyllithium or tert-butyllithium; or the like, but n-butyllithium is preferred.

The leaving group of the phosphorus compound having a leaving group, which is represented by $X^2$ in the scheme above, may be exemplified by a halogen atom such as chlorine or bromine; a sulfonyloxy group such as a methanesulfonyloxy group, a p-toluenesulfonyloxy group, a benzenesulfonyloxy group or a trifluoromethanesulfonyloxy group; an alkoxy group or aryloxy group such as a methoxy group, an ethoxy group, a butoxy group or a phenoxy group; or the like, but a halogen atom is preferred.

For the first step of in this method, the presence of a base is not essential, but the reaction of the second step is preferably performed in the presence of a base. The base used in these steps may be an inorganic base or an organic base, or a mixture thereof, and is not particularly limited. However, there may be mentioned carbonates of alkali metals or alkaline earth metals, such as lithium carbonate, sodium carbonate, potassium carbonate, rubidium carbonate, cesium carbonate, magnesium carbonate, calcium carbonate and barium carbonate; alkali metal alkoxides such as sodium methoxide, sodium ethoxide, sodium phenoxide, sodium tert-butoxide, potassium methoxide, potassium ethoxide, potassium phenoxide, potassium tert-butoxide, lithium methoxide, lithium ethoxide, lithium phenoxide and lithium tert-butoxide; hydroxides of alkali metals or alkaline earth metals, such as sodium hydroxide, potassium hydroxide, lithium hydroxide, barium hydroxide and potassium hydroxide; phosphates of alkali metals, such as lithium phosphate, potassium phosphate and sodium phosphate; amines such as trimethylamine, triethylamine, triisopropylamine, tricyclohexylamine, diethylamine, diethylamine and diisopropylamine; fluorides of alkali metals, such as lithium fluoride, potassium fluoride, sodium fluoride, cesium fluoride and rubidium fluoride; and the like. Among these, organic bases are preferred, and in particular, amines such as triethylamine and diisopropylamine are preferred.

The amount of the base used in the second step is preferably two-fold or more the amount in moles of the compound having phosphorus-nitrogen bonding. When the amount of the base is less than two-fold the amount in moles of the compound, the yield of the target compound may be lowered. When the base is added in large excess, the yield of the target compound is virtually not affected; however, since the post-treatment operations after completion of the reaction become complicated, a more preferred amount of the base is in the range of two- to ten-fold the amount in moles.

The reaction in the respective steps described above is preferably performed in the presence of a solvent. The solvent used may be a solvent which is inert to these reactions, and is not particularly limited, but there may be mentioned aliphatic organic solvents such as pentane, hexane, heptane and octane; alicyclic organic solvents such as cyclohexane and methylcyclohexane; aromatic organic solvents such as benzene, toluene and xylene; ether-based organic solvents such as diethyl ether, diisopropyl ether, dimethoxyethane, tetrahydrofuran, dioxane and dioxolane; and aprotic polar solvents such as acetonitrile, dimethylformamide, dimethylsulfoxide and hexamethylphosphotriamide. As preferred solvents, aromatic organic solvents such as benzene, toluene and xylene, or ether-based organic solvents such as diethyl ether, dimethoxyethane, tetrahydrofuran and dioxane may be mentioned.

Furthermore, the reactions in the respective steps described above are preferably performed in an atmosphere of inert gas such as nitrogen or argon, in view of the nature of the compounds dealt with.

The reaction temperature of the first step (reaction for generating phosphorus-nitrogen bonding) is in the range of −78° C. to 40° C., and preferably −50° C. to 25° C. The reaction time itself may vary depending on the reaction temperature, but is about 1 to 4 hours.

The reaction temperature of the second step (reaction with biaryldiol) is in the range of −20° C. to 40° C., and preferably −20° C. to 25° C. The reaction time itself may vary depending on the reaction temperature, but is about 3 to 16 hours. After completion of the reaction, the desired compound can be obtained by treating the reaction product according to general methods.

For the optically active ligand used in the present invention, it is acceptable to first react biaryldiol with $P(X^2)_3$, and subsequently react the product with a secondary amine or an alkali metal amide thereof, as in the method described in Tetrahedron, 56, 2865 (2000), Tetrahedron: Asymmetry, 9, 1179 (1998) or the like.

Additionally, although explanation is given, for convenience, for the cases of $R^1$, $R^2$, $R^3$ and $R^4$ in the scheme, the same holds true for the cases of $R^{1'}$, $R^{2'}$, $R^{3'}$ and $R^{4'}$.

The method of the present invention is characterized in that 1,4-conjugate addition of a methyl group to 2-cyclopentadecen-1-one is performed by means of a methylated organic metal in the presence of a copper catalyst, an enol anion scavenger and an optically active ligand represented by general formula (1), thus to produce an optically active 3-methyl-1-cyclopentadecene derivative represented by general formula (2). In this method, the above-described compounds can be used for the 2-cyclopentadecen-1-one, copper catalyst, enol anion scavenger and the optically active ligand represented by the general formula (1).

In this method of the present invention, 2-cyclopentadecen-1-one, a copper catalyst, an enol anion scavenger and an optically active ligand represented by general formula (1) may be simultaneously added and reacted, but preferably, there may be mentioned a method of performing a 1,4-conjugate addition reaction of a methyl group to 2-cyclopentadecen-1-one by means of a methylated organic metal in the presence of the copper catalyst and the optically active ligand represented by the general formula (1), and then adding an enol anion scavenger to the reaction mixture to produce an optically active 3-methyl-1-cyclopentadecene derivative represented by general formula (2). In the latter case, the 1,4-conjugate addition reaction of a methyl group by means of a methylated organic metal can be performed at a temperature near room temperature.

The methylated organic metal used in this method may be exemplified by dimethylzinc, methylmagnesium chloride, methylmagnesiumbromide, methylmagnesiumiodide, methyllithium, trimethylaluminum or the like. Preferred examples include dimethylzinc and the like.

The reaction solvent used in this method may be any solvent which does not participate in the reaction, and examples thereof include aliphatic hydrocarbon solvents such as pentane, hexane and heptane; aromatic hydrocarbon solvents such as toluene, xylene and mesitylene; ether-based solvents such as diethyl ether, diisopropyl ether, methyl tert-butyl ether, dibutyl ether, cyclopentyl methyl ether, 1,2-dimethoxyethane, tetrahydrofuran, 1,4-dioxane and 1,3-dioxolane; halogenated hydrocarbon solvents such as methylene chloride, dichloroethane and chlorobenzene; and the like. Among them, aliphatic hydrocarbon solvents, aromatic hydrocarbon solvents and ether-based solvents are preferred. These solvents may be used individually or in appropriate combination of two or more species.

The amount of use of the solvent is 1- to 200-fold, preferably 3- to 100-fold, and more preferably 5- to 30-fold the volume of 1 part by weight of 2-cyclopentadecen-1-one.

The amount of use of the copper catalyst in this method may be about 0.1 to 20% by mole, and preferably about 1.0 to 10% by mole, based on 1 mole of 2-cyclopentadecen-1-one.

The amount of use of the enol anion scavenger in this method is 1.0 to 5.0 moles, and preferably about 1.2 to 3.0 moles, based on 1 mole of 2-cyclopentadecenone.

The amount of use of the optically active ligand in this method is preferably 2-fold or more, and more preferably about 2-fold to 3-fold, the molar amount of the copper catalyst used.

Further, the amount of use of the methylated organic metal in this method is 1.0 to 5.0 moles, and preferably about 1.2 to 3.0 moles, based on 1 mole of 2-cyclopentadecenone.

The method for production is preferably carried out in an inert gas such as nitrogen or argon.

The reaction temperature in this method itself may vary depending on the reagents used, but may be in the range of about −80° C. to 50° C., and preferably in the range of about −30° C. to 30° C. In the case of performing the reaction by adding the enol anion scavenger after the 1,4-conjugate addition reaction, the 1,4-conjugate addition reaction can be performed at a temperature near room temperature. Also, the reaction time for this method is about 10 minutes to 20 hours, and preferably about 30 minutes to 10 hours.

After the completion of the reaction, the target product can be obtained using generally conducted operations such as extraction, distillation, recrystallization or various chromatographies.

Furthermore, in the method of the present invention, optically active muscone can be selectively produced by subjecting the enol moiety of the thus-obtained optically active 3-methylcyclopentadecene derivative represented by the following general formula (2):

[Chemical Formula 11]

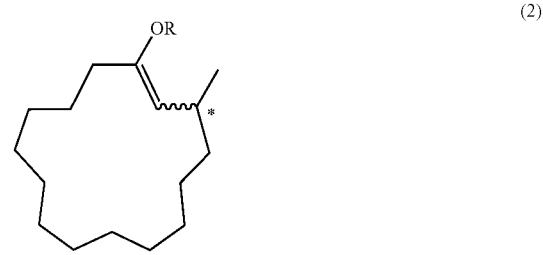

(2)

wherein R represents an enol anion scavenger residue; * represents an asymmetric carbon atom; and the broken line in the formula represents that the compound is a cis-isomer or trans-isomer, or a mixture thereof, to solvolysis.

As the method for solvolysis, a generally used solvolysis method for enols can be used. As such a method, for example, in the case where the enol derivative in the optically active 3-methyl-1-cyclopentadecene derivative represented by the formula (2) is an enol ester or an enol carbonate, there may be mentioned a method of reacting the enol derivative in a solvent using a basic catalyst. The basic catalyst used in this solvolysis may be exemplified by lithium hydroxide, sodium hydroxide, potassium hydroxide, magnesium hydroxide, calcium hydroxide, lithium carbonate, sodium carbonate, potassium carbonate, magnesium carbonate, calcium carbonate, sodium hydrogen carbonate, potassium hydrogen carbonate, lithium alkoxide (lithium methoxide, lithium ethoxide, lithium tert-butoxide, etc.), sodium alkoxide (sodium methoxide, sodium ethoxide, sodium tert-butoxide, etc.), potassium alkoxide (potassium methoxide, potassium ethoxide, potassium tert-butoxide, etc.), or the like. Among these, sodium hydroxide, potassium hydroxide, sodium methoxide, sodium ethoxide and the like are preferred. These basic catalysts may be used alone or as a mixture of two or more species.

Further, in the case where the enol derivative is an enol ether, a method of reacting the enol derivative in a solvent using an acidic catalyst may be mentioned. The acidic catalyst used in this solvolysis may be exemplified by hydrochloric acid, hydrobromic acid, sulfuric acid, phosphoric acid, methanesulfonic acid, p-toluenesulfonic acid, acetic acid, chloroacetic acid, trifluoroacetic acid, acidic ion exchange resins, or the like. Preferred acidic catalysts include hydrochloric acid, sulfuric acid, p-toluenesulfonic acid, and the like. These acidic catalysts may be used alone or as a mixture of two or more species.

Moreover, in the case where the enol derivative is a silyl enol ether, fluorine-based compounds such as boron trifluoride or a complex compound thereof, and fluorinated quaternary ammonium salts may be mentioned, in addition to the method of reacting the enol derivative in a solvent using the acidic catalyst described above. Also, the solvent used in the solvolysis may be a solvent in which solvolysis proceeds, and examples thereof include water; alcohols such as methanol, ethanol, isopropanol, n-butanol and benzyl alcohol; and solvent mixtures thereof. Among these, methanol and ethanol are preferred.

In addition, a co-solvent may be used, if necessary, in the present solvolysis. The co-solvent may be any so long as it does not participate in the reaction, and examples thereof include ether-based solvents such as diethyl ether, diisopropyl ether, methyl tert-butyl ether, cyclopentyl methyl ether, tetrahydrofuran, dimethoxyethane and dioxane; aliphatic hydrocarbon solvents such as hexane, heptane and octane; and aromatic solvents such as toluene and xylene.

The amount of use of the solvent is 0.5- to 100-fold the volume, and preferably 1- to 30-fold the volume, based on 1 part by weight of the optically active 3-methylcyclopentadecene derivative represented by the general formula (2). Also, the reaction is performed at a temperature of 0 to 200° C., and preferably about 20 to 100° C., and the reaction is allowed to continue for usually 10 minutes to 20 hours, and preferably about 30 minutes to 10 hours. Such reaction conditions may be appropriately varied depending on the type or amount of the solvent or catalyst used.

After completion of the reaction, the target product can be isolated by general post-treatments, using distillation, column chromatography or the like, as necessary.

EFFECT OF THE INVENTION

According to the present invention, an asymmetric methylation reaction can be performed through 1,4-addition of 2-cyclopentadecen-1-one using an optically active ligand which is easy to produce and has a relatively simple structure, and by scavenging the enol anions generated in the 1,4-addition reaction, as enol derivatives by an enol anion scavenger, the intermolecular side reactions of the generated enol anions can be suppressed. It is also possible to increase the substrate (2-cyclopentadecenone) concentration to a high concentration, to thus improve the reaction efficiency, and it is also possible to perform the 1,4-addition reaction at high temperatures. Furthermore, the optically active ligand of the present invention has high catalytic activity, and can efficiently allow the reaction to proceed in the presence of a small amount of catalyst. The present invention is to provide a method for producing a target optical isomer of high optical purity at a high yield, by such a simple method. The present invention is also to provide a novel compound which is effective in such asymmetric methylation reaction and easy to produce. Further, the ligand of the present invention is such that the amine moiety may have an asymmetric structure, and the structure of the two substituents present on the nitrogen atom of amine can be easily modified, making it possible to select a rich variety of substituent combinations in accordance with the reaction conditions.

BEST MODE FOR CARRYING OUT THE INVENTION

Hereinafter, the present invention will be described in more detail by way of Examples, but the present invention is not intended to be limited thereto.

The analyses in the present Examples were performed using the following analysis instruments.

| | |
|---|---|
| Optical rotation: | P-1020 (JASCO Corporation) |
| $^1$H-NMR: | DRX500 type (500 MHz) (Bruker, Inc.) (Internal standard substance: tetramethylsilane) |
| Infrared absorption spectroscopy (IR): | Nicolet Avatar 360 FT-IR (Nicolet Japan Co., Ltd.) |
| Mass spectroscopy (MS): | M-80B mass spectrometer (ionization voltage: 20 eV) (Hitachi, Ltd.) |
| : | PolarisQ iontraptype (Direct EI) (Thermoelectron Corp.) |
| Gas chromatography: | RTx-1 (RESTEX Corp.) |
| High performance liquid chromatography (HPLC): | CHIRALPAK AS-H (Daicel Chemical Industries, Ltd.) |

Example 1

Synthesis of O,O'—(R)-(1,1'-binaphthalene-2,2'-diyl)-N-benzyl-N—(R)-(1-p henylethyl)phosphoramidite (L-1) Represented by the Following Chemical Formula

[Chemical Formula 12]

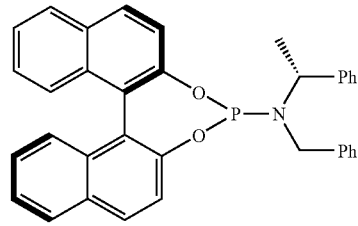

Under a nitrogen gas stream, a solution of 20 mL of THF and 1.05 g (5.0 mmol) of (R)-(+)-N-benzyl-N-(1-phenylethyl)amine was introduced to a 50-mL three-necked flask equipped with a thermometer and a dropping funnel, the solution was cooled to −50° C., and 3.2 mL (5.0 mmol) of n-butyllithium (1.58 M hexane solution) was added dropwise. After stirring the mixture at −50° C. for 1 hour, 6.8 g (50 mmol) of phosphorus trichloride was added, and the mixture was gradually warmed to room temperature, and then stirred for 2 hours. Subsequently, the solvent and phosphorus trichloride were removed under reduced pressure, and 20 mL of toluene was added to the residue. This toluene solution was cooled to −20° C., and a mixed solution of 1.43 g (5.0 mmol) of (R)-(+)-1,1-bi(2-naphthol), 2.53 g (25 mmol) of triethylamine and 10 mL of toluene was added dropwise. The mixed solution was gradually warmed to room temperature, and stirred for 16 hours. After completion of the reaction, the solids were filtered, and the filtrate was concentrated and purified by silica gel column chromatography, to obtain 1.8 g (3.42 mmol, yield 68%) of the title compound.

$^1$H-NMR (500 MHz, CDCl$_3$, δ); 1.68-1.70 (3H, m), 3.02 (1H, d, J=15.1 Hz), 4.03 (1H, d, J=15.1 Hz), 4.04-4.09 (1H, m), 7.02-7.99 (22H, m)

$^{31}$P (200 MHz, δ); 142.8

MS m/z: 525 (M$^+$) (5), 434(100), 420(10), 391(12), 315(8), 286(14), 253(4), 239(6), 105(5), 91(5), 79 (3)

Example 2

Synthesis of (R)-3-methyl-1-cyclopentadecenyl Propionate Represented by the Following Chemical Formula

[Chemical Formula 13]

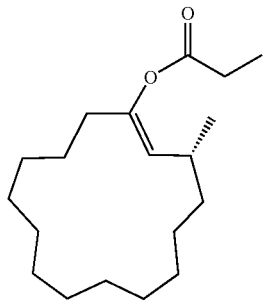

In a nitrogen atmosphere, 21.0 mg (0.04 mmol) of the optically active ligand obtained in Example 1, O,O'—(R)-(1,1'-binaphthalene-2,2'-diyl)-N-benzyl-N—(R)-(1-p henyleth-yl)phosphoramidite, 7.2 mg (0.02 mmol) of Cu(OTf)$_2$ and 7 mL of toluene were introduced into a 30-mL reaction flask equipped with a thermometer, and the mixture was stirred at room temperature for 30 minutes. 1.4 mL (2.8 mmol) of a toluene solution of dimethylzinc (2.0 mol/L) was added to the solution, and the mixture was stirred for 30 minutes. Subsequently, the solution was cooled to −20° C., and 0.29 g (2.2 mmol) of propionic anhydride and 0.44 g (2.0 mmol) of 2-(E)-cyclopentadecenone were added dropwise. After completion of the dropwise addition, the mixture was stirred for 2 hours, the reaction was stopped by adding a 5% aqueous solution of sulfuric acid, and liquid partition was performed. The organic layer obtained was washed with water, and the solvent was removed under reduced pressure, to obtain 0.8 g of a crude product. This crude product was purified by silica gel column chromatography, to obtain 0.53 g (1.80 mmol) of the title compound with a yield of 90%. The result of gas chromatographic analysis was E/Z=1.0/99.0.

$^1$H-NMR (500 MHz, CDCl$_3$, δ); 0.90 (3H, d, J=12.5 Hz), 1.07-1.15 (2H, m), 1.20 (3H, t, J=7.6 Hz), 1.26-1.40 (15H, m), 2.14-2.16 (1H, m), 2.30-2.39 (2H, m), 2.40 (2H, q, J=7.6), 4.77 (1H, d, J=9.6)

MS m/z: 293 (M$^+$) (5), 265(3), 238(90), 220(30), 209(27), 195(13), 180(11), 158(7), 142(7), 125(38), 117(28), 97(60), 84(55), 69(62), 57(100), 41 (37)

IR vmax (cm$^{-1}$): 2926, 2856, 1152 [α]$_D$=79.2 (c=1.0 in CHCl$_3$)

Example 3

Synthesis of (R)-Muscone Represented by the Following Formula

[Chemical Formula 14]

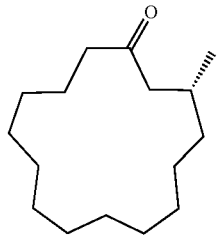

0.53 g (1.8 mmol) of (R)-3-methyl-1-cyclopentadecenyl propionate obtained in Example 2 and 20 g of toluene were introduced into a 30-mL recovery flask, and the mixture was stirred. 0.39 g (2.0 mmol) of a 28% methanol solution of sodium methoxide was added dropwise at 20° C., and then the mixture was stirred for 1 hour. Subsequently, a 5% aqueous solution of sulfuric acid was added to the reaction liquid, and then liquid partition was performed. The organic layer was washed with water, and then the solvent was removed under reduced pressure, to obtain 0.60 g of a crude product. This crude product was purified by silica gel column chromatography to obtain (R)-muscone with a yield of 97%. The optical purity was measured by high performance liquid chromatography, and the result was 86.1% ee.

Example 4

Synthesis of O,O'—(R)-(1,1'-binaphthalene-2,2'-diyl)-N-(1-naphthyl)methy 1-N—(R)-(1-phenyl-ethyl)phosphoramidite (L-2) Represented by the Following Chemical Formula

[Chemical Formula 15]

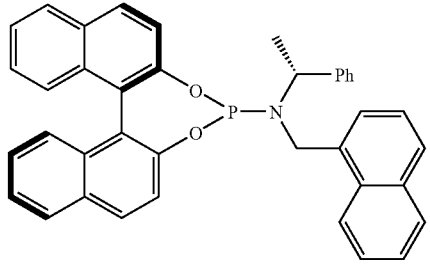

The same operation was performed in the same manner as in Example 1, except that (R)-(+)-N-benzyl-N-(1-phenyl-ethyl)amine of Example 1 was replaced with (R)—N-(1-naphthyl)methyl-N-(1-phenylethyl)amine, thus to obtain 2.07 g (3.6 mmol, yield 72%) of the title compound.

$^1$H-NMR (500 MHz, CDCl$_3$, δ); 1.73-1.76 (3H, m), 3.76 (1H, d, J=15.8 Hz), 4.10-4.54 (1H, m), 4.39 (1H, d, J=15.8 Hz), 7.02-8.00 (24H, m)

$^{31}$P (200 MHz, δ); 146.1

MS m/z: 575 (M⁺) (14), 470(22), 434(100), 391(11), 333 (4), 315(10), 268(25), 246(22), 239(13), 167(7), 149(20), 141(65), 115(16), 91(13), 79 (5)

Example 5

Synthesis of (R)-Muscone

In a nitrogen atmosphere, 23.0 mg (0.04 mmol) of the optically active ligand obtained in Example 4, O,O'—(R)-(1,1'-binaphthalene-2,2'-diyl)-N-(1-naphthyl)methy l-N—(R)-(1-phenylethyl)phosphoramidite, 7.2 g (0.02 mmol) of Cu(OTf)$_2$ and 7 mL of toluene were introduced into a 30-mL reaction flask, and the mixture was stirred at room temperature for 30 minutes. 1.4 mL (2.8 mmol) of a toluene solution of dimethylzinc (2.0 mol/L) was added to the solution, and the mixture was stirred for 30 minutes. Subsequently, the reaction solution was cooled to −20° C., and 0.29 g (2.2 mmol) of propionic anhydride and 0.44 g (2.0 mmol) of 2-(E)-cyclopentadecenone were added dropwise. After completion of the dropwise addition, the mixture was stirred for 2 hours, the reaction was stopped by adding a 5% aqueous solution of sulfuric acid, liquid partition was performed, and then the organic layer was washed twice with water. 0.39 g (2.0 mmol) of a 28% methanol solution of sodium methoxide was added to this organic layer, the mixture was stirred at room temperature for 30 minutes, and then a 5% aqueous solution of sulfuric acid was added to stop the reaction. The organic layer was washed with water, and the solvent was removed under reduced pressure, to obtain 0.50 g of crude (R)-muscone. This crude product was purified by silica gel column chromatography, to obtain (R)-muscone with a yield of 84.8%. The optical purity was measured by high performance liquid chromatography, and the result was 89.2% ee.

Example 6

Synthesis of O,O'—(R)-(1,1'-binaphthalene-2,2'-diyl)-N-(2-methoxybenzyl)-N—(R)-(1-phenylethyl)phosphoramidite (L-3) Represented by the Following Chemical Formula

[Chemical Formula 16]

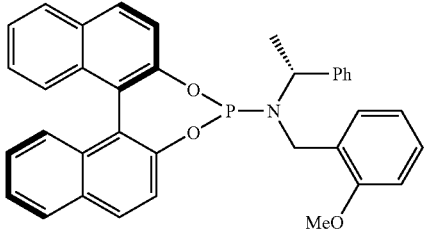

The same operation was performed in the same manner as in Example 1, except that (R)-(+)-N-benzyl-N-(1-phenylethyl)amine of Example 1 was replaced with (R)—N-(2-methoxybenzyl)-N-(1-phenylethyl)amine, thus to obtain 1.89 g (3.40 mmol, yield 68%) of the title compound.

$^1$H-NMR (500 MHz, CDCl$_3$, δ); 1.70-1.72 (3H, m), 3.52 (3H, s), 3.58-3.71 (2H, m), 4.15-4.19 (1H, m), 6.65-7.98 (21H, m) $^{31}$P (200 MHz, δ); 146.2

Example 7

Synthesis of O,O'—(R)-(1,1'-binaphthalene-2,2'-diyl)-N-(3,4-methylenedioxybenzyl)-N—(R)-(1-phenylethyl)phosphoramidite (L-4) Represented by the Following Chemical Formula

[Chemical Formula 17]

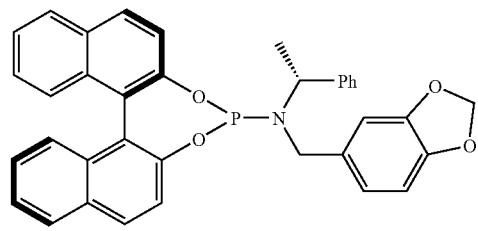

(R)-(+)-N-benzyl-N-(1-phenylethyl)amine of Example 1 was replaced with (R)—N-(3,4-methylenedioxybenzyl)-N-(1-phenylethyl)amine, and the same operation was performed to obtain 1.79 g (3.15 mmol, yield 63%) of O,O'—(R)-(1,1'-binaphthalene-2,2'-diyl)-N-(3,4-methylenedioxybenzyl)-N—(R)-(1-phenylethyl)phosphoramidite.

$^1$H-NMR (500 MHz, CDCl$_3$, δ); 1.68-1.71 (3H, m), 2.91 (1H, d, J=14.8 Hz), 3.92 (1H, d, J=14.8 Hz), 4.07-4.12 (1H, m), 5.86-5.89 (2H, m), 6.48-8.01 (20H, m)

$^{31}$P-NMR (200 MHz, δ); 142.5

MS m/z: 569 (M⁺)(1), 464(20), 434(100), 391(7), 333(3), 315(7), 268(15), 239(5), 135(13), 105(8), 77 (5)

Example 8

Synthesis of O,O'—(R)-(1,1'-binaphthalene-2,2'-diyl)-N-cyclohexylmethyl-N—(R)-(1-phenylethyl)phosphoramidite (L-5) Represented by the Following Chemical Formula

[Chemical Formula 18]

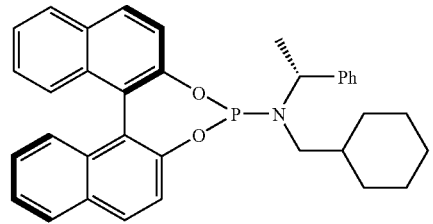

(R)-(+)-N-benzyl-N-(1-phenylethyl) amine of Example 1 was replaced with (R)—N-cyclohexylmethyl-N-(1-phenylethyl) amine, and the same operation was performed to obtain 2.07 g (3.9 mmol, yield 78%) of O,O'—(R)-(1,1'-binaphthalene-2,2'-diyl)-N-cyclohexylmethyl-N—(R)-(1-phenylethyl)phosphoramidite.

$^1$H-NMR (500 MHz, CDCl$_3$, δ); 0.90-1.55 (11H, m), 1.72-1.74 (3H, m), 2.18-2.21 (1H, m), 2.45-2.49 (1H, m), 4.43-4.48 (1H, m), 6.99-7.97 (17H, m)

$^{31}$P-NMR (200 MHz, δ); 148.2

MS m/z: 531 (M⁺) (11), 448(12), 434(17), 420(15), 391 (60), 372(20), 344(15), 333(25), 315(85), 295(72), 268(100), 252(30), 239(27), 105(28), 79 (10)

Example 9

Synthesis of O,O'—(R)-(1,1'-binaphthalene-2,2'-diyl)-N-(2-methylbenzyl)-N—(R)-(1-phenylethyl) phosphoramidite (L-6) Represented by the Following Chemical Formula

[Chemical Formula 19]

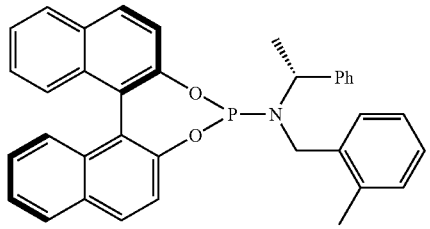

(R)-(+)-N-benzyl-N-(1-phenylethyl) amine of Example 1 was replaced with (R)—N-(2-methylbenzyl)-N-(1-phenylethyl)amine, and the same operation was performed to obtain 1.89 g (3.5 mmol, yield 70%) of O,O'—(R)-(1,1'-binaphthalene-2,2'-diyl)-N-(2-benzyl)-N—(R)-(1-phenylethyl)phosphoramidite.

$^1$H-NMR (500 MHz, CDCl$_3$, δ); 1.71 (3H, s), 1.77-1.79 (3H, m), 3.25 (1H, d, J=16.0 Hz), 3.82 (1H, d, J=16.0 Hz), 4.08-4.13 (1H, m), 6.94-7.98 (21H, m)

$^{31}$P-NMR (200 MHz, δ); 146.2

MS m/z: 539 (M$^+$) (2), 524(18), 434(100), 420(7), 391(7), 333(5), 315(5), 268(17), 239(8), 105(8), 79 (6)

Example 10

Synthesis of O,O'—(R)-(1,1'-binaphthalene-2,2'-diyl)-N-(2-naphthyl)methyl-N—(R)-(1-phenylethyl) phosphoramidite (L-7) Represented by the Following Chemical Formula

[Chemical Formula 20]

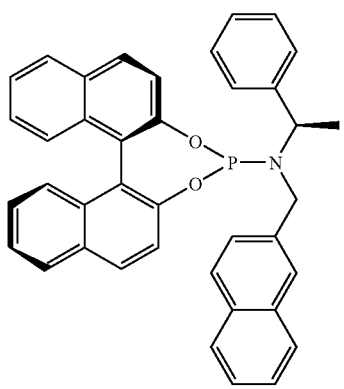

(R)-(+)-N-benzyl-N-(1-phenylethyl) amine of Example 1 was replaced with (R)—N-(2-naphthyl)methyl-N-(1-phenylethyl)amine, and the same operation was performed to obtain 1.30 g (2.25 mmol, yield 56%) of O,O'—(R)-(1,1'-binaphthalene-2,2'-diyl)-N-(2-naphthyl)methyl 1-N—(R)-(1-phenylethyl)phosphoramidite.

$^1$H-NMR (500 MHz, CDCl$_3$, δ); 1.67-1.70 (3H, m), 3.20 (1H, d, J=15.0 Hz), 4.08-4.12 (1H, m), 4.19 (1H, d, J=15.0 Hz), 7.06-8.03 (24H, m)

$^{31}$P (200 MHz, δ); 143.0

MS m/z: 575 (M$^+$) (10), 470(30), 434(100), 391(11), 333 (8), 315(7), 268(25), 252(7), 239(6), 141(65), 115 (16)

Example 11

Synthesis of O,O'—(R)-(1,1'-binaphthalene-2,2'-diyl)-N-(2,6-dimethylbenz yl)-N—(R)-(1-phenylethyl)phosphoramidite (L-8) Represented by the Following Chemical Formula

[Chemical Formula 21]

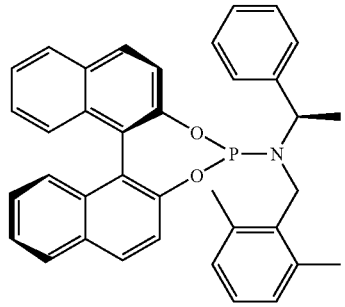

(R)-(+)-N-benzyl-N-(1-phenylethyl) amine of Example 1 was replaced with (R)—N-(2,6-dimethylbenzyl)-N-(1-phenylethyl)amine, and the same operation was performed to obtain 0.90 g (1.66 mmol, yield 40%) of O,O'—(R)-(1,1'-binaphthalene-2,2'-diyl)-N-(2,6-dimethylbenz yl)-N—(R)-(1-phenylethyl)phosphoramidite.

$^1$H-NMR (500 MHz, CDCl$_3$, δ); 1.55-1.57 (3H, m), 1.95 (6H, s), 3.50 (1H, d, J=13.7 Hz), 3.98-4.02 (1H, m), 4.12 (1H, d, J=13.7 Hz), 6.79-7.91 (20H, m)

$^{31}$P (200 MHz, δ); 148.0

MS m/z: 553 (M$^+$) (1), 538(4), 434(35), 333(5), 315(6), 268 (45), 252(15), 239(28), 226(8), 180(5), 132(8), 119(100), 105(90), 91(93), 79(50), 65 (13)

Example 12

Synthesis of O,O'—(R)-(1,1'-binaphthalene-2,2'-diyl)-N-(2,4-dimethylbenz yl)-N—(R)-(1-phenylethyl)phosphoramidite (L-9) Represented by the Following Chemical Formula

[Chemical Formula 22]

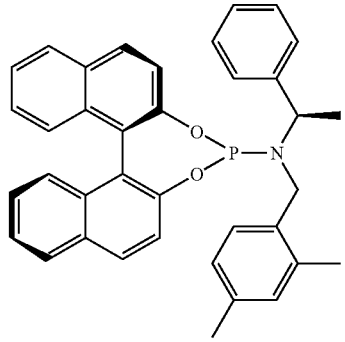

(R)-(+)-N-benzyl-N-(1-phenylethyl) amine of Example 1 was replaced with (R)—N-(2,4-dimethylbenzyl)-N-(1-phenylethyl)amine, and the same operation was performed to obtain 1.39 g (2.60 mmol, yield 65%) of O,O'—(R)-(1,1'-binaphthalene-2,2'-diyl)-N-(2,4-dimethylbenz yl)-N—(R)-(1-phenylethyl)phosphoramidite.

$^1$H-NMR (500 MHz, CDCl$_3$, δ) ; 1.62 (3H, s), 1.68-1.70 (3H, m), 2.15 (3H, s), 3.13 (1H, d, J=15.9 Hz), 3.71 (1H, d, J=15.9 Hz), 3.99-4.04 (1H, m), 6.69-7.90 (20H, m) $^{31}$P (200 MHz, δ); 146.3

MS m/z: 553 (M+) (2), 538(5), 434(63), 391(5), 333(5), 315(6), 268(50), 252(15), 239(30), 226(8), 180(5), 166(6), 149(7), 132(5), 119(100), 105(55), 91(78), 79(32), 65 (8)

Example 13

Synthesis of O,O'—(R)-(1,1'-binaphthalene-2,2'-diyl)-N-(2-ethylbenzyl)-N—(R)-(1-phenylethyl) phosphoramidite (L-10) Represented by the Following Chemical Formula

[Chemical Formula 23]

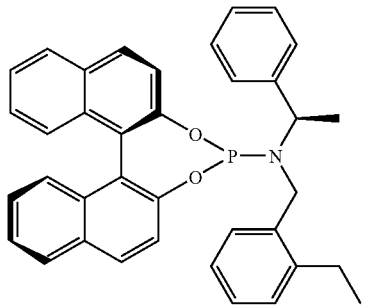

(R)-(+)-N-benzyl-N-(1-phenylethyl) amine of Example 1 was replaced with (R)—N-(2-ethylbenzyl)-N-(1-phenylethyl)amine, and the same operation was performed to obtain 1.31 g (2.37 mmol, yield 59%) of O,O'—(R)-(1,1'-binaphthalene-2,2'-diyl)-N-(2-ethylbenzyl)-N—(R)-(1-phenylethyl) phosphoramidite.

$^1$H-NMR (500 MHz, CDCl$_3$, δ); 0.46 (3H, t, J=7.6), 1.70-1.72 (3H, m), 1.92-2.03 (2H, m), 3.21 (1H, d, J=15.3 Hz), 3.77 (1H, d, J=15.3 Hz), 3.99-4.04 (1H, m), 6.87-7.90 (21H, m)

$^{31}$P (200 MHz, δ); 146.5

MS m/z: 553 (M+) (3), 524(70), 434(100), 420(48), 391 (13), 333(15), 315(15), 268(85), 252(28), 239(36), 226(10), 180(5), 166(7), 152(15), 132(5), 117(55), 105(53), 91(55), 79(27), 65 (5)

Example 14

Synthesis of O,O'—(R)-(1,1'-binaphthalene-2,2'-diyl)-N-(2-biphenyl)methy 1-N—(R)-(1-phenyl-ethyl)phosphoramidite (L-11) Represented by the Following Chemical Formula

[Chemical Formula 24]

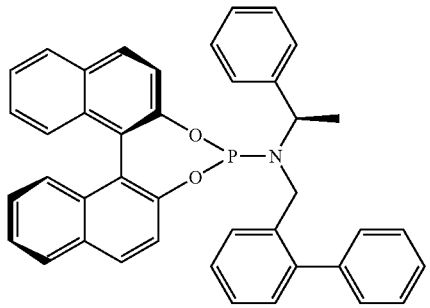

(R)-(+)-N-benzyl-N-(1-phenylethyl) amine of Example 1 was replaced with (R)—N-(2-biphenyl)methyl-N-(1-phenylethyl) amine, and the same operation was performed to obtain 1.12 g (1.86 mmol, yield 46%) of O,O'—(R)-(1,1'-binaphthalene-2,2'-diyl)-N-(2-biphenyl)methyl-N—(R)-(1-phenylethyl)phosphoramidite.

$^1$H-NMR (500 MHz, CDCl$_3$, δ); 1.63-1.66 (3H, m), 3.03 (1H, d, J=16.2 Hz), 3.74 (1H, d, J=16.2 Hz), 3.79-3.83 (1H, m), 6.37-7.91 (26H, m)

$^{31}$P (200 MHz, δ); 146.6

MS m/z: 601 (M+) (1), 496(5), 434(100), 420(2), 391(12), 333(8), 315(8), 268(44), 252(14), 239(20), 226(5), 180(6), 165(100), 152(36), 132(5), 105(34), 77 (13)

Example 15

Synthesis of O,O'—(R)-(1,1'-binaphthalene-2,2'-diyl)-N-(indan-1-yl)-N—(R)-(1-phenylethyl)phosphoramidite (L-12) Represented by the Following Chemical Formula

[Chemical Formula 25]

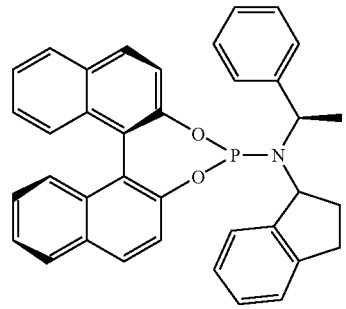

(R)-(+)-N-benzyl-N-(1-phenylethyl) amine of Example 1 was replaced with N-(indan-1-yl)-N—(R)-(1-phenylethyl) amine, and the same operation was performed to obtain 0.88 g (1.60 mmol, yield 40%) of O,O'—(R)-(1,1'-binaphthalene-2,2'-diyl)-N-(indan-1-yl)-N—(R)-(1-phenylethyl)phosphoramidite.

$^1$H-NMR (500 MHz, CDCl$_3$, δ) ; 1.64-1.65 (3H, m), 2.15-2.20 (1H, m), 2.47-2.51 (1H, m), 2.64-2.71 (1H, m), 2.95-3.01 (1H, m), 4.42-4.45 (1H, m), 4.60-4.66 (1H, m), 7.13-7.66 (21H, m)

$^{31}$P (200 MHz, δ); 151.5

MS m/z: 552 (M+) (100), 464(20), 434(90), 332(40), 315 (15)

Example 16

Synthesis of O,O'—(R)-(1,1'-binaphthalene-2,2'-diyl)-N-(2-methylbenzyl)-N—(R)-(1-cyclohexylethyl)phosphoramidite (L-13) Represented by the Following Chemical Formula

[Chemical Formula 26]

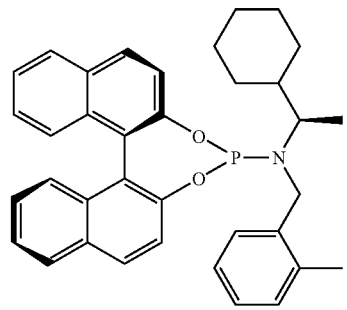

(R)-(+)-N-benzyl-N-(1-phenylethyl) amine of Example 1 was replaced with N-(2-methylbenzyl)-N—(R)-(1-cyclohexylethyl)phosphoramidite, and the same operation was performed to obtain 1.07 g (1.96 mmol, yield 49%) of O,O'—

(R)-(1,1'-binaphthalene-2,2'-diyl)-N-(2-methylbenzyl)-N—(R)-(1-cyclohexylethyl)phosphoramidite.

$^1$H-NMR (500 MHz, CDCl$_3$, δ) 0.93-1.08 (2H, m), 1.09-1.30 (4H, m), 1.32 (3H, d, J=7 Hz) 1.52-1.93 (5H, m), 1.95 (1H, s), 2.82-2.91 (1H, m), 3.52 (1H, d, J=13.7 Hz), 3.93 (1H, d, J=13.7 Hz), 6.90-7.95 (16H, m)

$^{31}$P (200 MHz, δ); 148.7

MS m/z: 544 (M$^+$) (7), 530(100), 462(85), 434(8), 420(15), 404(4), 333(10), 315(60), 268(34), 252(14), 239(7), 105(50), 79 (15)

Example 17

Synthesis of O,O'—(R)-(1,1'-binaphthalene-2,2'-diyl)-N-(9-anthryl)methyl —N—(R)-(1-phenylethyl) phosphoramidite (L-14) Represented by the Following Chemical Formula

[Chemical Formula 27]

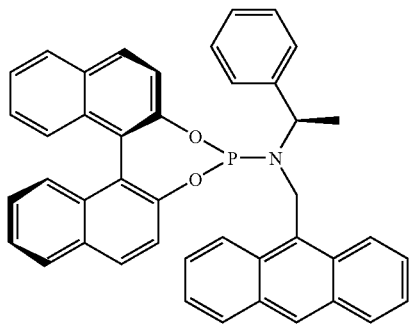

(R)-(+)-N-benzyl-N-(1-phenylethyl) amine of Example 1 was replaced with (R)—N-(9-anthryl)methyl-N-(1-phenylethyl)amine, and the same operation was performed to obtain 0.750 g (1.20 mmol, yield 30%) of O,O'—(R)-(1,1'-binaphthalene-2,2'-diyl)-N-(9-anthryl)methyl —N—(R)-(1-phenylethyl)phosphoramidite.

$^1$H-NMR (500 MHz, CDCl$_3$, δ); 1.48-1.50 (3H, m), 3.90-3.98 (1H, m), 4.47 (1H, d, J=14.1 Hz), 5.11 (1H, d, J=14.1 Hz), 7.16-8.32 (26H, m)

$^{31}$P (200 MHz, δ); 151.5

MS m/z: 625 (M$^+$)(63), 520(70), 434(100), 349(13), 333 (8), 315(15), 268(26), 252(8), 239(7), 205(10), 191(62), 178 (10), 165(6), 105(55), 79 (32)

Examples 18 to 29

Synthesis of Optically Active Muscone

Synthesis of optically active muscone was performed according to the operation of Example 5, by replacing the ligand and the reaction temperature as indicated in the following Table 1. The results are presented in the Table 1 below.

TABLE 1

| Examples | Ligand | Temperature (° C.) | Yield (%) | Optical Purity (ee %) | Configuration |
|---|---|---|---|---|---|
| 18 | L-3 | −20 | 86.0 | 86.3 | (R) |
| 19 | L-4 | −20 | 84.5 | 85.5 | (R) |
| 20 | L-5 | −20 | 88.7 | 87.2 | (R) |
| 21 | L-6 | −20 | 96.5 | 92.1 | (R) |

TABLE 1-continued

| Examples | Ligand | Temperature (° C.) | Yield (%) | Optical Purity (ee %) | Configuration |
|---|---|---|---|---|---|
| 22 | L-6 | 0 | 91.8 | 90.4 | (R) |
| 23 | L-7 | −20 | 85.9 | 85.0 | (R) |
| 24 | L-8 | −20 | 86.7 | 84.4 | (R) |
| 25 | L-9 | −20 | 84.4 | 92.2 | (R) |
| 26 | L-10 | −20 | 75.2 | 91.8 | (R) |
| 27 | L-11 | −20 | 70.6 | 90.3 | (R) |
| 28 | L-12 | −20 | 96.6 | 82.0 | (S) |
| 29 | L-13 | −20 | 85.0 | 89.5 | (R) |

Comparative Example 1

Synthesis was performed in the same manner as in Example 21, except that 0.29 g (2.2 mmol) of propionic anhydride, which was the enol anion scavenger of Example 21, was not used, and 0.300 g (1.26 mmol, yield 63.1%) of (R)-muscone was obtained.

As a result, it was found that the method of the present invention using an enol anion scavenger is a method that can suppress side reactions and obtain the target product with a high yield.

Comparative Example 2

In the method (see Example 4 of Patent Document 5) described in Patent Document 5 (Korean Unexamined Patent Application Publication No. 2000-49811), mesomer-derived 4-(cis-2,6-dimethylpiperidine)-(R)-dinaphthodioxaphosphepine represented by the following formula:

[Chemical Formula 28]

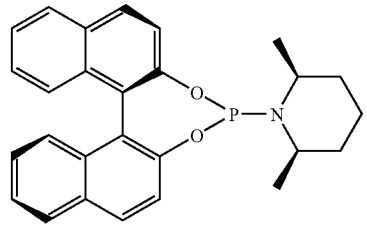

is used as the ligand. Using this ligand, the amounts of the copper compound, ligand and dimethylzinc were changed to the amounts of the method of the present invention, and the experiment was performed. That is, in the method described in Patent Document 5, 5.54% by mole of the copper compound is used, 10.0% by mole of the ligand is used, and 4.0 equivalents of dimethylzinc, which is a methylating agent, is used. However, the method described in Patent Document 5 was performed by changing these amounts of catalysts to 1.0% by mole and 2.0% by mole, respectively, and the amount of dimethylzinc to 1.4 equivalents, according to the method of the present invention. However, the solvent toluene was used in a 20-fold amount relative to the raw material 2-cyclopentadecen-1-one, as in the method of the present invention.

As a result, the yield of (R)-muscone did not exceed 60.7%. Also, the optical purity was measured, and the result was 79.5% ee.

As can be seen, the method of the present invention was found to exhibit high activity with small amounts of catalysts.

INDUSTRIAL APPLICABILITY

The optically active muscone obtained by the present invention is useful in, for example, the field of fragrances, and the method of the present invention has industrial applicability as a method for production thereof. Further, the compound of the present invention is useful as the ligand in the 1,4-addition reaction of α,β-unsaturated ketones, and has industrial applicability.

The invention claimed is:

1. A method for producing optically active 3-methylcyclopentadecanone, the method comprising reacting 2-cyclopentadecen-1-one with a methylated organic metal in the presence of a copper catalyst, an enol anion scavenger and an optically active phosphoramidite represented by general formula (1):

[Chemical Formula 29]

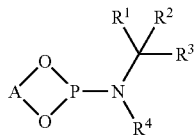
(1)

wherein $R^1$ and $R^2$ each independently represent a hydrogen atom or an alkyl group having 1 to 4 carbon atoms; $R^3$ represents a cycloalkyl group having 3 to 10 carbon atoms which may be substituted, or an aryl group which may be substituted; $R^4$ represents an alkyl group having 1 to 10 carbon atoms, a cycloalkyl group having 3 to 10 carbon atoms which may be substituted, an aryl group which may be substituted, or an aralkyl group which may be substituted; and A represents an optically active biaryldiyl group, to perform a reaction of 1,4-conjugate addition of a methyl group, thus to produce an optically active 3-methyl-1-cyclopentadecene derivative represented by general formula (2):

[Chemical Formula 30]

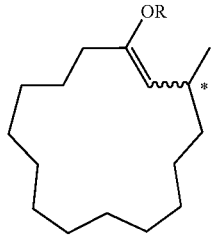
(2)

wherein R represents an enol anion scavenger residue; * represents an asymmetric carbon atom; and the broken line in the formula represents that the compound is a cis-isomer, a trans-isomer, or a mixture thereof, and subsequently subjecting the derivative to solvolysis.

2. The method according to claim 1, wherein the optically active 3-methylcyclopentadecanone is 3-(R)-methylcyclopentadecanone.

3. A method for producing an optically active 3-methyl-1-cyclopentadecene derivative represented by general formula (2):

[Chemical Formula 32]

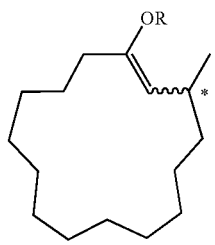
(2)

wherein R represents an enol anion scavenger residue; * represents an asymmetric carbon atom; and the broken line in the formula represents that the compound is a cis-isomer, a trans-isomer, or a mixture thereof, the method comprising performing a reaction of 1,4-conjugate addition of a methyl group to 2-cyclopentadecen-1-one by means of a methylated organic metal, in the presence of a copper catalyst, an enol anion scavenger and optically active phosphoramidite represented by general formula (1):

[Chemical Formula 31]

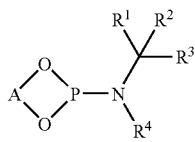
(1)

wherein $R^1$ and $R^2$ each independently represent a hydrogen atom or an alkyl group having 1 to 4 carbon atoms; $R^3$ represents a cycloalkyl group having 3 to 10 carbon atoms which may be substituted, or an aryl group which may be substituted; $R^4$ represents an alkyl group having 1 to 10 carbon atoms, a cycloalkyl group having 3 to 10 carbon atoms which may be substituted, an aryl group which may be substituted, or an aralkyl group which may be substituted; and A represents an optically active biaryldiyl group.

4. The method according to any one of claims 1 to 3, wherein the method for producing the optically active 3-methyl-1-cyclopentadecene derivative represented by general formula (2) is a method for producing the derivative by adding an enol anion scavenger to the optically active enol anions which are generated by reacting 2-cyclopentadecen-1-one with a methylated organic metal in the presence of a copper catalyst and an optically active ligand represented by the general formula (1) to perform a reaction of 1,4-conjugate addition of a methyl group.

* * * * *